United States Patent [19]
Yamamoto et al.

[11] Patent Number: 5,717,076
[45] Date of Patent: Feb. 10, 1998

[54] METAL-ENCAPSULATED FULLERENE DERIVATIVE COMPOUND OF AND METHOD FOR MAKING THE DERIVATIVE

[75] Inventors: Kazunori Yamamoto, Naka-gun; Hideyuki Funasaka; Takeshi Takahashi, both of Hitachinaka; Toshiyasu Suzuki, Tsukuba; Yusei Maruyama, Tachikawa; Tatsuhisa Kato, Okazaki; Takeshi Akasaka, Tsukuba, all of Japan

[73] Assignee: Doryokuro Kakunenryo Kaihatsu Jigyodan, Tokyo, Japan

[21] Appl. No.: 711,649

[22] Filed: Sep. 10, 1996

[30] Foreign Application Priority Data

Sep. 19, 1995 [JP] Japan ................................ 7-240087

[51] Int. Cl.$^6$ ............... C01B 31/00; C07F 5/00; C09B 45/38
[52] U.S. Cl. ............... 534/558; 534/11; 534/15; 534/662; 427/213.3; 556/1
[58] Field of Search ............... 534/558, 662, 534/11, 15; 556/1; 427/213.3

[56] References Cited

PUBLICATIONS

Chem. Phys. Lett., vol. 216, No. 1,2, Dec. 24, 1993, "Isolation and Characterization of the Metallofullerene LaC82", Koichi Kikuchi et al., pp. 67–71.
J. Am. Chem. Soc., vol. 115, No. 23, 1993, "Electrochemical Properties of La@C82", Toshiyasu Suzuki et al., pp. 11006–11007.
J. Phys. Chem., vol. 98, No. 8, 1994, "Isolation of an ESR–Active Metallofullerene of La@C82", Kazunori Yamamoto et al., pp. 2008–2011.
J. Phys. Chem., vol. 98, No. 49, 1994, "Isolation and Characterization of ESR–Active La@C82 Isomer", Kazunori Yamamoto et al., pp. 12831–12833.
Angew. Chem. Int. Ed. Engl., vol. 34, No. 10, 1995, "Electrochemistry and AB Initio Study of the Dimetallofullerene La2@C80", Toshiyasu Suzuki et al., pp. 1094–1096.
Nature, vol. 357, May 7, 1992, "Encapsulation of a Scandium Trimer in C82", Hisanori Shinohara et al., pp. 52–54.
J. Phys. Chem., vol. 97, No. 17, 1993, "Isolation and Spectroscopic Properties of SC2@C74, and Sc2@C84", Hisanori Shinohara et al., pp. 4259–4261.
J. Phys. Chem., vol. 98, No. 35, Sep. 1, 1994, "Spectroscopic Properties of Isolated Sc3@C82 Metallofullerene", Hisanori Shinohara et al., pp. 8597–8599.
Chem. Phys. Lett., vol. 190, No. 190, No. 5, Mar. 13, 1992, "XPS Probes of Carbon–Cages Metals", J.H. Weaver et al., pp. 460–464.
J. Am. Chem. Soc., vol. 116, No. 20, 1994, "Characterization of the Isolated Y@C82", Koichi Kikuchi et al., pp. 9367–9368.
J. Phys. Chem., vol. 96, No. 17, 1992, "Endohedral Rare–Earth Fullerene Complexes", R. L. Whetten et al., pp. 6869–6871.
J. Phys. Chem., vol. 97, No. 26, 1993, "Studies of Metallofullerene Primary Soots by Laser and Thermal Desorption Mass Spectrometry", R.S. Ruoff et al., pp. 6801–6805.

Chem. Phys. Lett., vol. 232, Jan. 13, 1995, "Magnetic Properties of Gd@c82 Metallofullerene", Hideyuki Funasaka et al., pp. 273–277.
J. Phys. Chem. vol. 99, No. 7, 1995 "Magnetic Properties of Rare–Earth Metallofullerenes", Hideyuki Funasaka et al., pp. 1826–1830.
Science, vol. 257, Sep. 18, 1992, "Uranium Stabilization of C28: A Tetravalent Fullerene", R.E. Smalley et al., pp. 1661–1664.
J. Am. Chem. Soc., vol. 110, 1988, "Photophysics of Metal Complexes of Spheroidal Carbon Shells", R.E. Smalley et al., pp. 4464–4465.
Chem. Phys. Lett., vol. 207, No. 4,5,6, May 28, 1993, "The Electronic Structure of Ca@c60", R.E. Smalley et al., pp. 354–359.
Z. Phys., vol. D26, 1993, "Photoelectron Spectroscopy and Electronic Structure of Ca@c60", R.E. Smalley et al., pp. 297–299.
J. Chem. Soc., Chem. Commun., 1993, "Calcium Inside C60 and C70–From Coorongite, A Precursor of Torbanite", K.J. Fisher et al., pp. 941–942.
J. Chem. Soc., Chem. Commun., 1993, "Endohedral Barium and Strontium Fullerenes", K.J. Fisher et al., pp. 1361–1363.
J. Am. Chem. Soc., vol. 114, 1992, "A Novel FeC60 Adduct in the Solid State", C.N.R. Rao et al., pp. 2272–2273.
Indian J. Chem., vol. 31, May 1992, "Investigations of Iron Adducts of C60 Novel FeC60 in the Solid State with Fe Inside the C60 Cage", C.N.R. Rao et al., pp. F17–F21.
Nature, vol. 363,Jun. 17, 1993, "Cobalt–Catalysed Growth of Carbon Nanotubes with Single–Atomic–Layer Walls", D.S. Bethune, et al., pp. 605–607.
Gendaikagaku, No. 253, Apr. 1992, M.A. Ciufolini, pp. 12–19.
Kagaku, vol. 50, Jun. 1995, Shigeru Yamago, pp. 12–16.
J. Am. chem. Soc., vol. 115, No. 15, 1993, "Inhibition of the HIV–1 Protease by Fullerene Derivatives: Model Building Studies and Experimental Verification", S.H. Friedman et al., pp. 6506–6509.
J. Phys. Chem., vol. 95, No. 20, 1991, "Fullerenes with Metals Inside", R. Smalley et al., pp. 7564–7568.
Nature, vol. 374, 1995, "Exohedral Adducts of LaC82", T. Akasaka et al., p. 600.
J. Chem. Soc., Chem. Commun., 1995, "Exohedral Derivatization of an Endohedral Metallofullerene Gd@C82", T. Akasaka et al., p. 1343.

*Primary Examiner*—Floyd D. Higel
*Attorney, Agent, or Firm*—Oliff & Berridge, P.L.C.

[57] ABSTRACT

There are provided a derivative of a metal-encapsulated fullerene having application as a functional material, superconducting material, electronics material or pharmaceutical material, and a method of synthesizing this derivative. The derivative of a metal-encapsulated fullerene having the following structure is synthesized by adding a substituted diazomethane to a metal-encapsulated fullerene and denitrifying in a solvent.

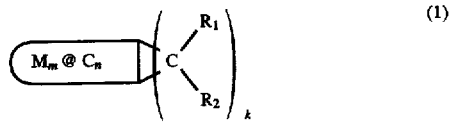

(1)

8 Claims, 5 Drawing Sheets

10 G

2 G

METAL-ENCAPSULATED FULLERENE DERIVATIVE COMPOUND OF AND METHOD FOR MAKING THE DERIVATIVE

BACKGROUND OF THE INVENTION

1. Field of the Invention

This invention relates to a useful metal-encapsulated fullerene compound having application as a functional material, a superconducting material, an electronics material or a pharmaceutical material.

2. Description of the Related Art

An all-carbon fullerene is a recently discovered carbon allotrope typified by Buckminster fullerene $C_{60}$, and it has attracted attention in recent years because of its unique cage structure. After discovery of macroscopic preparations of all-carbon fullerenes in 1990, various physical and chemical properties of the fullerenes were clarified, and since many derivatives of all-carbon fullerene have now been synthesized, nowadays they are applied to electrical conductors, semiconductors and pharmaceutical products. Many reports about application of all-carbon fullerenes and their derivatives have appeared in the literature (Gendaikagaku, No. 253, April 1992, pp. 12–19, and Kagaku, Vol. 50, June 1995, pp. 12–16), and in particular, reports of biological activity have emerged for derivatives of all-carbon fullerene (J. Am. Chem. Soc., 1993, Vol. 115, p. 6506) which have led to further research.

A metal-encapsulated fullerene is a new material closely related to an all-carbon fullerene. This material is comprised of an ordinary fullerene cage and a metal atom incorporated into inside of its cage structure. The physical and chemical properties of metal-encapsulated fullerenes Mm @Cn, can be controlled by changing their encapsulated elements, suggesting many potential applications. After the invention of a method for macroscopic synthesis of lanthanum-encapsulated fullerenes $La_m@C_n$, (R. et al., J. Phys. Chem. 1991, Vol. 95, p.7564), intensive research is now being carried out. According to Smalley's report, it is possible to produce one-lanthanum-encapsulated fullerene $La@C_n$ with n=36–122, two-lanthanum-encapsulated fullerenes $La_2@Cn$ up to n=110, and three-lanthanum-encapsulated fullerenes $La_3@C_n$ up to n=98. Although there is essentially no higher limit, there is a lower limit for the value of n in $M_m@C_n$ fullerenes, and it is thought that the limit depends on the size In the case of $La@C_{82}$ a method has been described for and number of encapsulated metals or metal ions.

In the case of $La@C_{82}$, a method has been described for obtaining a pure sample and its characterizations have been reported (K. Kikuchi et al., Chem. Phys. Lett. 1993, Vol. 216, p. 67 and J. Am. Chem. Soc. 1994, Vol. 116, p. 9367; T. Suzuki et al., J. Am. Chem. Soc. 1993, Vol. 115, p. 11006; K. Yamamoto et al., J. Phys. Chem. 1994, Vol. 98, p. 2008 and J. Phys. Chem. 1994, Vol. 98, p. 12831). In the case of fullerenes encapsulating two lanthanum atoms, the characterization of $La_2@C_{80}$ has been reported (T. Suzuki et al., Angew. Chem. Int. Ed. Engl. 1995, Vol. 34, p. 1094).

The synthesis of scandium-encapsulated fullerenes, $Sc_m@C_n$, (m=1–3), is reported by H. Shinohara in Nature 1992, Vol. 357, p. 52. The separation methods are described for $Sc_2@C_n$ (n=74, 82, 84) in J. Phys. Chem. 1993, Vol. 97, p. 4259, and for $Sc_3@C_{82}$ in J. Phys. Chem. 1994, Vol. 98, p. 8597.

The first synthesis of yttrium-encapsulated fullerenes, $Y_m@C_n$, was reported by J. Weaver et al. (Chem. Phys. Lett. 1992, Vol. 190, p. 460), and the characterization of $Y@C_{82}$ was described by K. Kikuchi et al. in J. Am. Chem. Soc. 1994, vol. 116, p. 9367.

The production and extraction of lanthanoid-encapsulated fullerenes, $M_m@C_n$ (M=Ce, Nd, Sm, Eu, Gd, Tb, Dy, Ho, Er) are described by R. L. Whetten et al. in J. Phys. Chem. 1992, Vol. 96, p. 6869, and the production of other lanthanoid-encapsulated fullerenes, $M_m@C_n$ (M=Pr, Eu, Yb, Lu) is reported by R. S. Ruoff et al. in J. Phys. Chem. 1993, vol. 97, P. 6801. Of these, the isolation and characterization of $Gd@C_{82}$ were reported by H. Funasaka et al. in Chem. Phys. Lett. 1995, Vol. 232, p. 273 and J. Phys. Chem. 1995, Vol. 99, p. 1826. As to an actinoid-encapsulated fullerene, the synthesis of uranium-encapsulated fullerenes $U_m@C_n$ (m=1–2, n=28–80) is reported by R. Smalley et al. in Science 1992, Vol. 257, p. 1661.

In the case of alkali-metal-encapsulated fullerenes, potassium and cesium have been reported. The production of potassium-encapsulated fullerenes, $K@C_n$, is reported by R. Smalley et al. in J. Am. Chem. Soc. 1988, Vol. 110, p. 4464, and of cesium-encapsulated fullerenes, $Cs@C_n$, by R. Smalley et al. (J. Am. Chem. Soc. 1988, Vol. 110, p. 4464).

Fullerenes encapsulating an alkaline earth metal have been reported for calcium, strontium and barium. The production and extraction of a calcium-encapsulated fullerene, $Ca@C_{60}$, was first performed by R. Smalley et al. (Chem. Phys. Lett. 1993, Vol. 207, p. 354 and Z. Phys. 1993, Vol. D26, p. 297), after which the production of other $Ca@C_n$ fullerenes was confirmed by K. J. Fisher et al. (J. Chem. Soc., Chem. Commun. 1993, p. 941). The production of strontium-encapsulated fullerenes, $Sr_m@C_n$, and barium-encapsulated fullerenes, $Ba_m@C_n$, was reported by K. J Fisher et al. (J. Chem. Soc., Chem. Commun. 1993, p. 1361).

As an example of fullerenes encapsulating a transition metal, the synthesis of an iron-encapsulated fullerene, $Fe@C_{60}$, is reported by C. N. R. Rao et al. (J. Am. Chem. Soc, 1992, Vol. 114, p. 2272, and Indian J. Chem. 1992, Vol. 31, p. F17). The first synthesis of a cobalt-encapsulated fullerene, $Co@C_{60}$, is described by D. S. Bethune et al. in Nature 1993, Vol. 363, p. 605.

(Metal-Encapsulated Fullerene Derivatives)

As can be seen from the above examples, various metal atoms have so been reported to be capable of forming encapsulated fullerenes, most of these reports concerning methods of production and separation, and characterization of pure metal-encapsulated fullerenes. Using derivatives of all-carbon fullerenes, it was discovered that these fullerenes have biological activity, and it was therefore expected that metal-encapsulated fullerenes also would find application in the biochemical and medical fields. In this case, however, it is necessary to enhance their solubility in water to increase physiological affinity. For this purpose, metal-encapsulated fullerene derivatives having hydrophilic groups must be synthesized as in the case of all-carbon fullerenes.

Until now, no metal-encapsulated fullerene derivatives had successfully been synthesized, and the method of synthesizing them was unclear. Consequently, no reports have yet appeared in the literature concerning their biological activity. For the same reason, moreover, these metal-encapsulated fullerenes or metal-encapsulated fullerene compounds are not at present being used in the manufacture of functional materials, superconductors, electronics materials or pharmaceuticals. Considering the fact that a large number of chemical reactions are known for all-carbon fullerenes, it would appear that metal-encapsulated fullerenes have poorer reactivity than fullerene or a different type of reactivity.

Hence, whereas a great number of derivatives are known for all-carbon fullerene itself, no derivatives were known for metal-encapsulated fullerenes. Recently, however, T. Akasaka et al. reported a method of synthesizing an organosilicon derivative by adding a disilirane to the double bond of a metal-encapsulated fullerene (Nature 1995, Vol. 374, p. 600 and J. Chem. Soc., Chem. Commun. 1995, p. 1343). This report discloses, for the first time, a method of synthesizing a metal-encapsulated fullerene derivative, and it therefore provides one solution to the aforesaid problems. However, the atom directly bonded to the cage of the metal-encapsulated fullerene synthesized by this method is a "hetero" atom (i.e. silicon). From the viewpoint of stability of the derivative, therefore, it would be more desirable to bond carbon directly to the fullerene cage because carbon makes a shorter, stronger bond.

SUMMARY OF THE INVENTION

This invention, which was conceived in view of the above problems, therefore aims to provide a metal-encapsulated fullerene derivative in which a carbon atom is directly bonded to the fullerene cage.

As a result of intensive studies, the inventors discovered that a substituted methylene addition compound could be synthesized by reacting a substituted diazomethane with a metal-encapsulated fullerene, and thereby arrived at the present invention.

This invention is a derivative of a metal-encapsulated fullerene compound having the following structure:

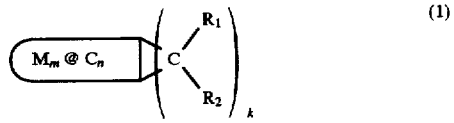

(1)

where M is an encapsulated metal atom,
m is an integer from 1 to 3,
n is an even number from 28 to 200,
k is an integer from 1 to 4, and
$R_1$, $R_2$ are hydrogen, an alkyl group, an aryl group or a group in which these groups have been substituted, but comprise no active hydrogen.

According to this invention, the metal M encapsulated in the metal-encapsulated fullerene derivative represented by the aforesaid formula (1) is chosen from a group comprising alkali metals, alkaline earth metals, transition elements, lanthanoid elements and actinoid elements.

The method of synthesizing the metal-encapsulated fullerene derivative according to this invention involves the cycloaddition reaction (i.e., cyclization by addition reaction) of a diazomethane or substituted diazomethane having the structure shown below, followed by a denitrification reaction. These two reactions have the effect of adding a substituted methylene group to the metal-encapsulated fullerene, thereby obtaining a metal-encapsulated fullerene derivative in which a carbon atom is directly bonded to the fullerene cage. The denitrification reaction takes place after the cycloaddition reaction without any need of further operations.

(2)

Herein, $R_1$, $R_2$ are hydrogen, an alkyl group, an aryl group or a group in which these groups have been substituted, but comprise no active hydrogen.

In the case of a highly reactive reagent such as diazomethane ($R_1$, $R_2$=H), the reaction temperature is sufficient in the vicinity of ambient temperature, however when $R_1$ or $R_2$ is an aryl group, the temperature must be set slightly higher. In general, to react a metal-encapsulated fullerene $M_m@C_n$ with a substituted diazomethane, the fullerene may be mixed with a solution of the diazomethane in a pyrex glass reaction vessel for example, and the temperature raised to 30°–100° C. The fact that the temperature of the reaction system can be raised to about 100° C. without a denitrification reaction of the diazomethane is clearly a new discovery, and is thought to be a unique phenomenon of reactions with metal-encapsulated fullerenes.

It is preferable to remove water or alcohol from the reaction system completely, moreover it is desirable to perform the reaction after removing gas by freeze degassing.

In this reaction, 1–10 mole parts of diazomethane or substituted diazomethane are used for 1 mole of metal-encapsulated fullerene. The number of methylenes added may be controlled by adjusting the amount of diazomethane and the reaction time. For example, to obtain a 1:1 addition product, the blending ratio may be 1:1, whereas to add two or more methylene groups, a large excess of diazomethane must be used relative to the amount of metal-encapsulated fullerene. The solvent used in this reaction may be an aromatic hydrocarbon solvent such as benzene, toluene, xylene or mesitylene, or a halogenated aromatic hydrocarbon solvent such as chlorobenzene, dichlorobenzene, trichlorobenzene or chloronaphthalene.

In this reaction, the cycloaddition compound shown below is sysnthesized first, and following this addition reaction, nitrogen ($N_2$) is eliminated easily from the cycloaddition compound giving rise to the methylene addition compound (1). In the compound (1) so obtained, carbon is directly bonded to the fullerene cage of the metal-encapsulated fullerene, and therefore the compound has high stability.

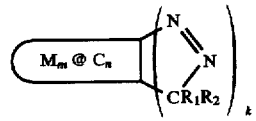

This invention represents the first attempt at introducing a side chain wherein carbon is directly bonded to the metal-encapsulated fullerene cage. In previous work, both fullerene derivatives having a side chain wherein carbon was directly bonded to a fullerene cage of all-carbon fullerenes encapsulating no metals, and metal-encapsulated fullerene derivatives which did not have a side chain wherein carbon was directly bonded to the metal-encapsulated fullerene cage, had already been produced. But no metal-encapsulated fullerene derivatives comprising such a side chain had ever been synthesized. If the conventional reaction method using diazomethane (wherein diazomethane ($N_2CR_1R_2$) is decomposed using ultraviolet light to generate methylene ($CR_1R_2$) which is then added) is applied directly in an attempt to introduce a side chain in the metal-encapsulated fullerene, no addition compound can be obtained. On the other hand, by performing a cycloaddition reaction of a predetermined diazomethane derivative in a selected solvent and then performing a denitrification as according to this invention, methylene can be introduced. In any event, if it is attempted to decompose a substituted diazomethane using ultraviolet light to convert it to a substituted methylene and then perform a reaction as according to the prior art, the metal-encapsulated fullerene derivative of this invention cannot be obtained.

It may be expected that for the addition compound according to the synthesizing method of this invention, both addition compounds across the 6-ring-6-ring junction and the 5-ring-6-ring junction are obtained.

DESCRIPTION OF THE PREFERRED EMBODIMENTS

Figures 1A, 1B, 1C, 1D, 1E:
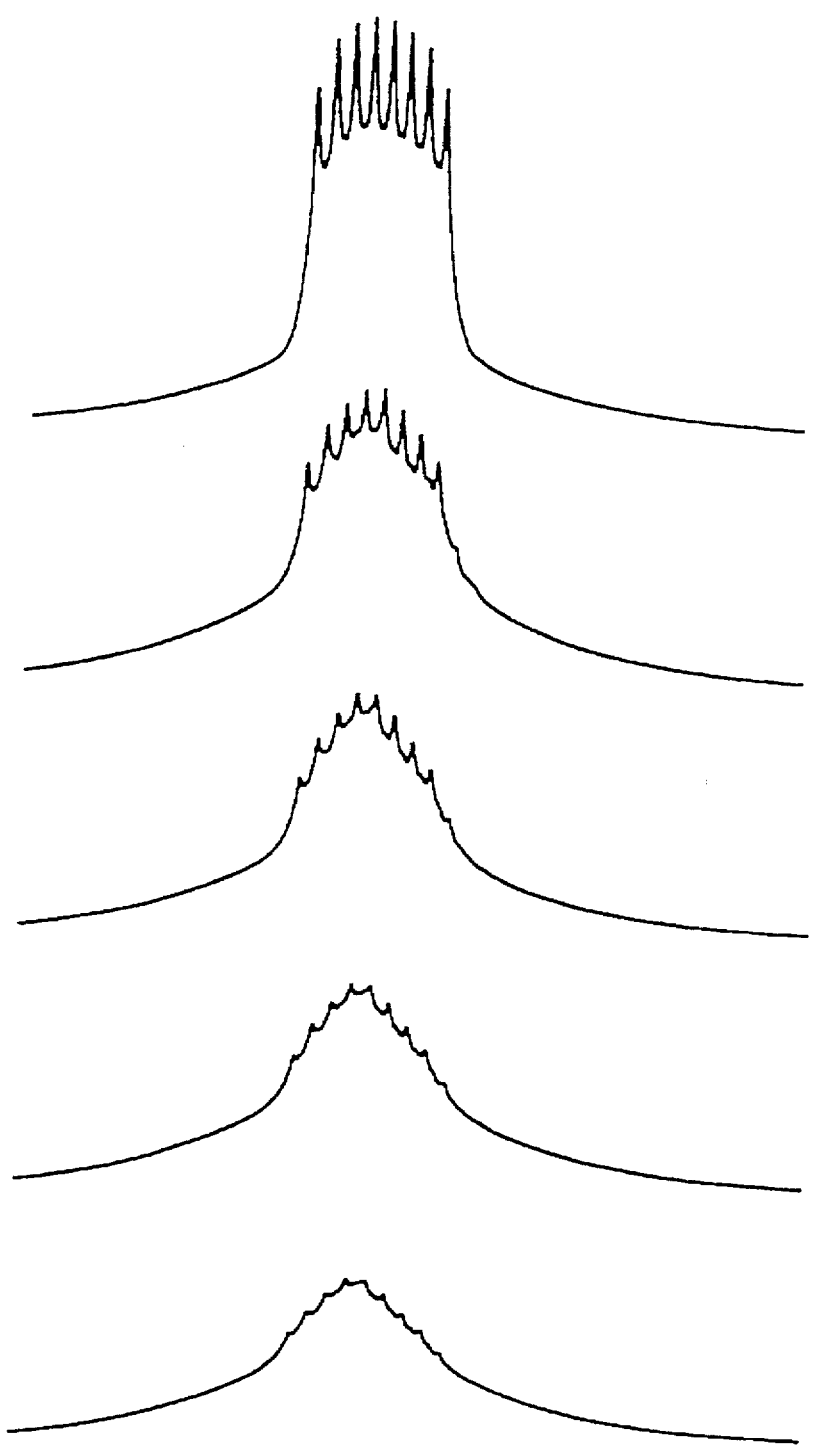
FIGS. 1(A)–1(E) are diagrams an electron spin resonance absorption spectrum illustrating the process in which compound (3) is formed (from 0 to 210 minutes). In the figures the horizontal axis is magnetic field strength, and the vertical axis is absorption intensity.

As stated hereinabove, many metal-encapsulated fullerenes are already known. As this invention concerns an addition reaction to the double bond of fullerene in order to synthesize the corresponding addition compound, it is evident that the metal-encapsulated fullerene compounds according to the present invention can be synthesized in the case of any metal introduced into fullerenes, and is not limited to the metals given below as examples. It may therefore be applied to fullerenes encapsulating any of the metals cited in the literature.

In the metal-encapsulated fullerene compound derivatives according to this invention, the substituent groups $R_1$, $R_2$ may be chosen as desired. The substituent groups $R_1$, $R_2$, which may be different, are hydrogen, alkyl, aryl or these groups containing substituents. Various functional groups may also be added to the side chain at a later stage. It may for example be conjectured that the metal-encapsulated fullerene compound would be soluble in water and have biological activity if carboxyl groups or hydroxyl groups were introduced in the side chain, as these groups have high physiological affinity. If the encapsulated metal is gadolinium, the fullerene compound may be used as a magnetic resonance relaxation reagent for MRI as in the case of other gadolinium chelates. Gadolinium ion is toxic, however whereas metal ions easily dissociate in chelates and the toxicity of gadolinium ion presents a problem, there is no metal dissociation in metal-encapsulated fullerene compounds so this problem does not occur.

The metal-encapsulated fullerene compound derivative according to this invention may also be applied in the biochemical and medical fields. This is due to the fact that such a derivative having physiological affinity may be synthesized by introducing a stable, hydrophilic side chain according to the method of this invention, and this derivative may also be produced in large quantity. For the same reasons, it may be expected that these metal-encapsulated fullerenes or derivatives of metal-encapsulated fullerene compounds may be used in the development and manufacture of functional materials, superconducting materials, electronics materials or pharmaceuticals.

For example in missile therapy of cancer using radioactive elements, the fullerene part of a metal-encapsulated fullerene compound derivative could play an important role as a vehicle for various radioactive elements. In order to investigate the biological activity of a substance and use it in the treatment for cancer, it is however necessary to enhance its solubility in water so as to increase its physiological affinity.

EXAMPLES

This invention will now be described in more detail with reference to specific examples.
(Example: Synthesis of Diphenylmethylene Addition Compound of Lanthanum-Encapsulated Fullerene, $La@C_{82}$ $(CPh_2)_n$, where n=1–4 and Ph is phenyl)

A toluene solution (20 ml) of $La@C_{82}$ (1 mg) and diphenyldiazomethane, $N_2CPh_2$ (1 mg), was placed in a quartz glass tube, and after removing gas by freeze degassing, an addition reaction was performed at 60° C. To monitor the progress of the addition reaction, time dependence was measured on an electron spin resonance absorption spectrum on which only paramagnetic molecules were observed.

As a result, the data shown in FIGS. 1(A)–1(E) and FIGS. 2(A)–s(E) were obtained. FIGS. 1(A)–1(E) or an electron spin resonance absorption spectrum, and FIGS. 2(A)–2(E) are the differential of the absorption intensity in FIGS. 1(A)–1(E). The change with time was measured by taking observations at (A) 0 min, (B) 30 min, (C) 90 min, (D) 150 min and (E) 210 min.

In the figures, (A) is the spectrum of $La@C_{82}$, which is the starting material. Due to spectral splitting with the lanthanum atom nucleus, there is a group of eight equally spaced peaks. This signal is attenuated exponentially with time indicating consumption of starting material due to addition of diazomethane (FIGS. 1(A)–1(E), FIGS. 2(A)–2(E)). It is also seen that the intensity of another group of eight peaks having a slightly different splitting interval increases (FIG. 2(B), (C)), and is then attenuated after a certain time (FIG. 2(D), (E)).

Figure 2A:
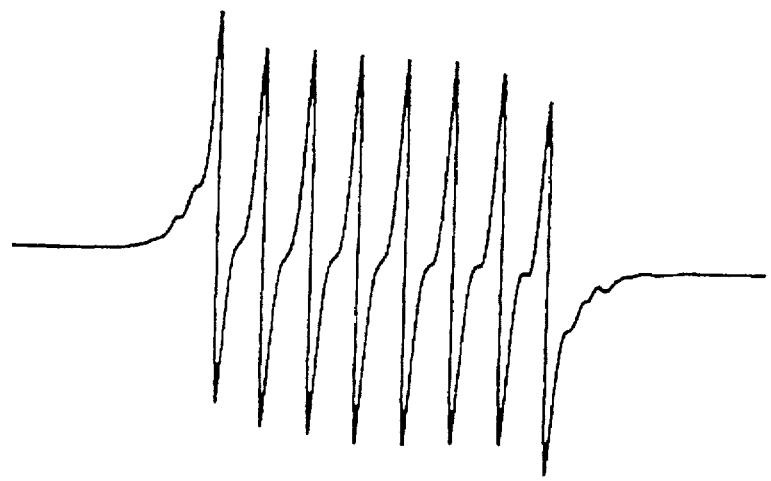
FIGS. 2(A)–2(E) are diagrams of an electron spin resonance absoprtion spectrum (differential) illustrating the process in which compound (3) is formed (from 0 to 210 minutes). In the figures, the horizontal axis is magnetic field strength, and the vertical axis is the differential of the absorption intensity.
Figure 2B:
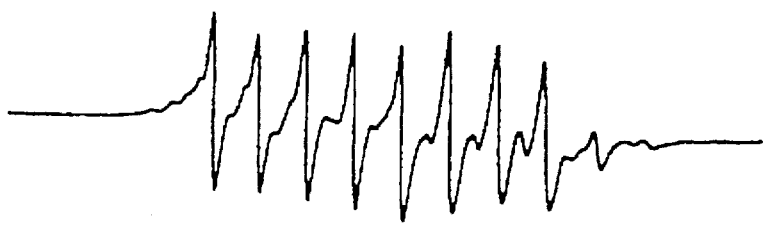
Figure 2C:
Figure 2D:
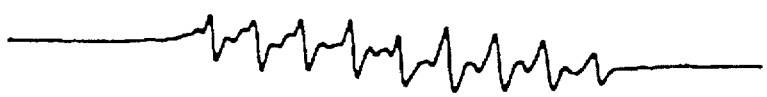
Figure 2E:

By observing the total absorption intensity in FIGS. 1(A)–1(E) it is evident that although there are a large number of paramagnetic molecules even after 210 minutes has elapsed, the intensity of the differential spectrum (FIG. 2(E)) apparently decreases due to superposition of absorptions. It was also confirmed from a simulation of the electron spin resonance absorption spectrum (not shown), FIG. 2(E) comprises at least six groups of eight peaks. These are probably due to structural isomers in which one diphenylmethylene ($CPh_2$) has added to different positions of $La@C_{82}$. From the mass spectra (FIGS. 3–5) of the product after 210 minutes, (E), it is clear that a compound (3) is produced in which 1–4 phenylmethylenes ($CPh_2$) have added to $La@C_{82}$.

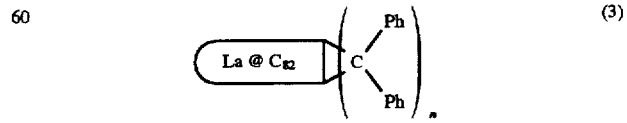

(3)

where n is an integer from 1 to 4.

Figure 3:
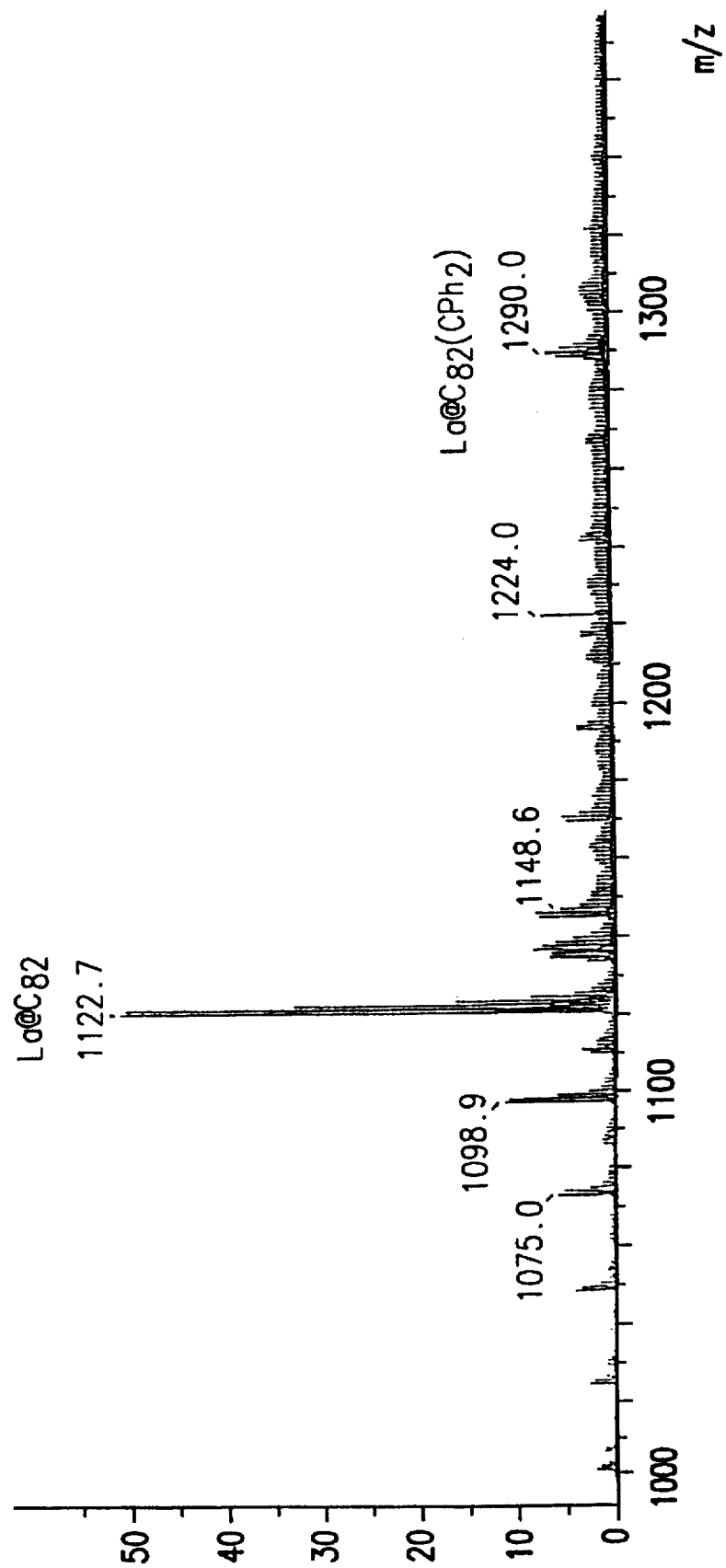
FIG. 3 is a diagram of a mass spectrum (mass range m/e=1000–1370) of a reaction product comprising compound (3) (at 210 minutes). In the figure, the horizontal axis is mass number and the vertical axis is relative ion intensity.

In the mass spectrum of FIG. 3 (mass range m/e= 1000–1370), molecular ion peaks due to a 1:1 adduct were observed from 1289 to 1292, and reference peaks due to La@$C_{82}$, the starting material, were observed from 1123 to 1125. This confirms the production of the compound La@$C_{82}$C$Ph_2$.

Figure 4:
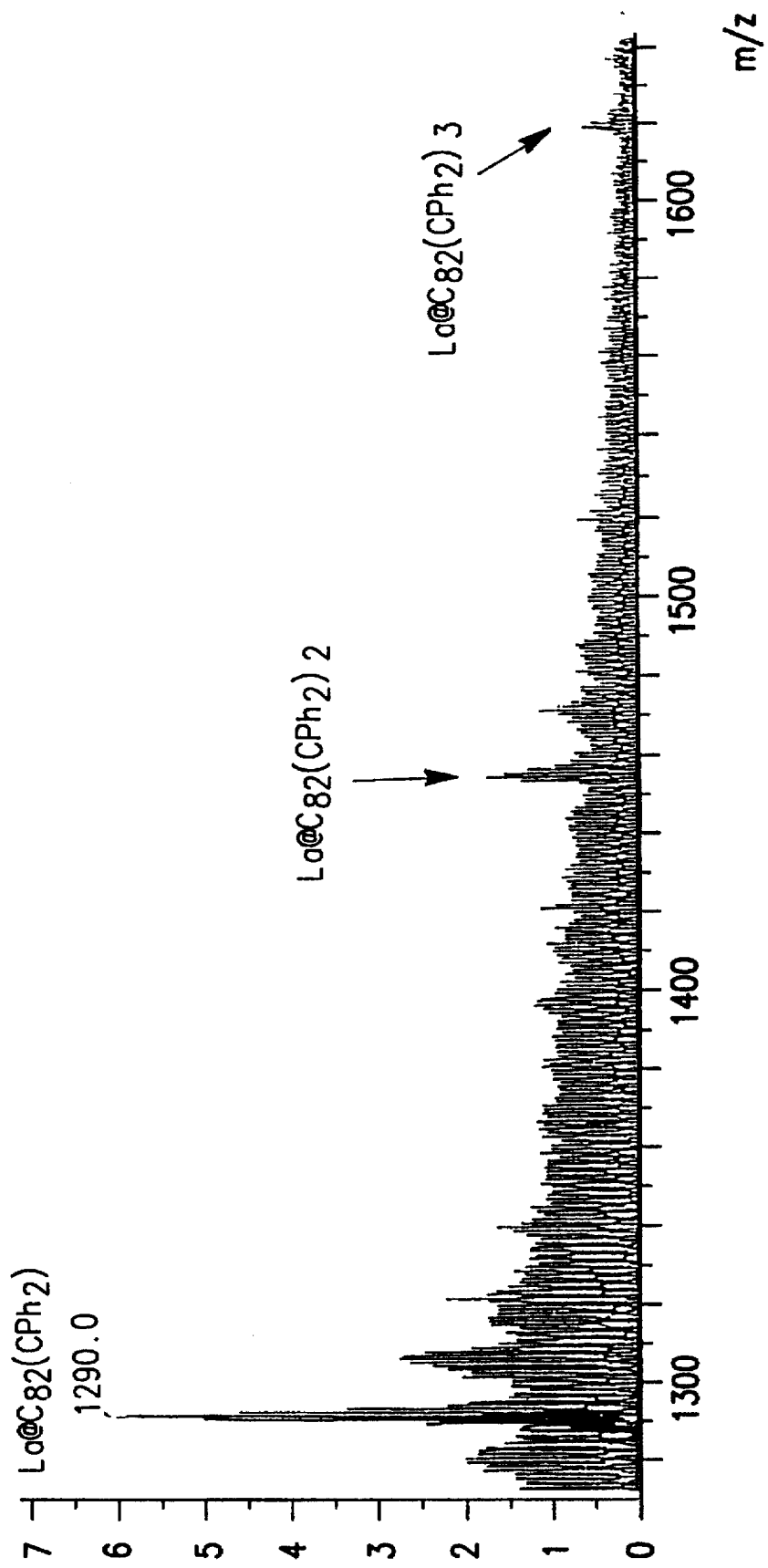
FIG. 4 is a diagram of a mass spectrum (mass range m/e=1270–1640) of a reaction product comprising compound (3) (at 210 minutes). In the figure, the horizontal axis is mass number and the vertical axis is relative ion intensity.

In the mass spectrum of FIG. 4 (mass range m/e= 1270–1640), in addition to the molecular ion peaks of the 1:1 adduct, molecular ion peaks due to a 1:2 adduct were observed from 1455 to 1459, and molecular ion peaks due to a 1:3 adduct were observed from 1621 to 1625. This confirms the production of the compounds La@$C_{82}$(C$Ph_2$)$_2$ and La@$C_{82}$(C$Ph_2$)$_3$.

Figure 5:
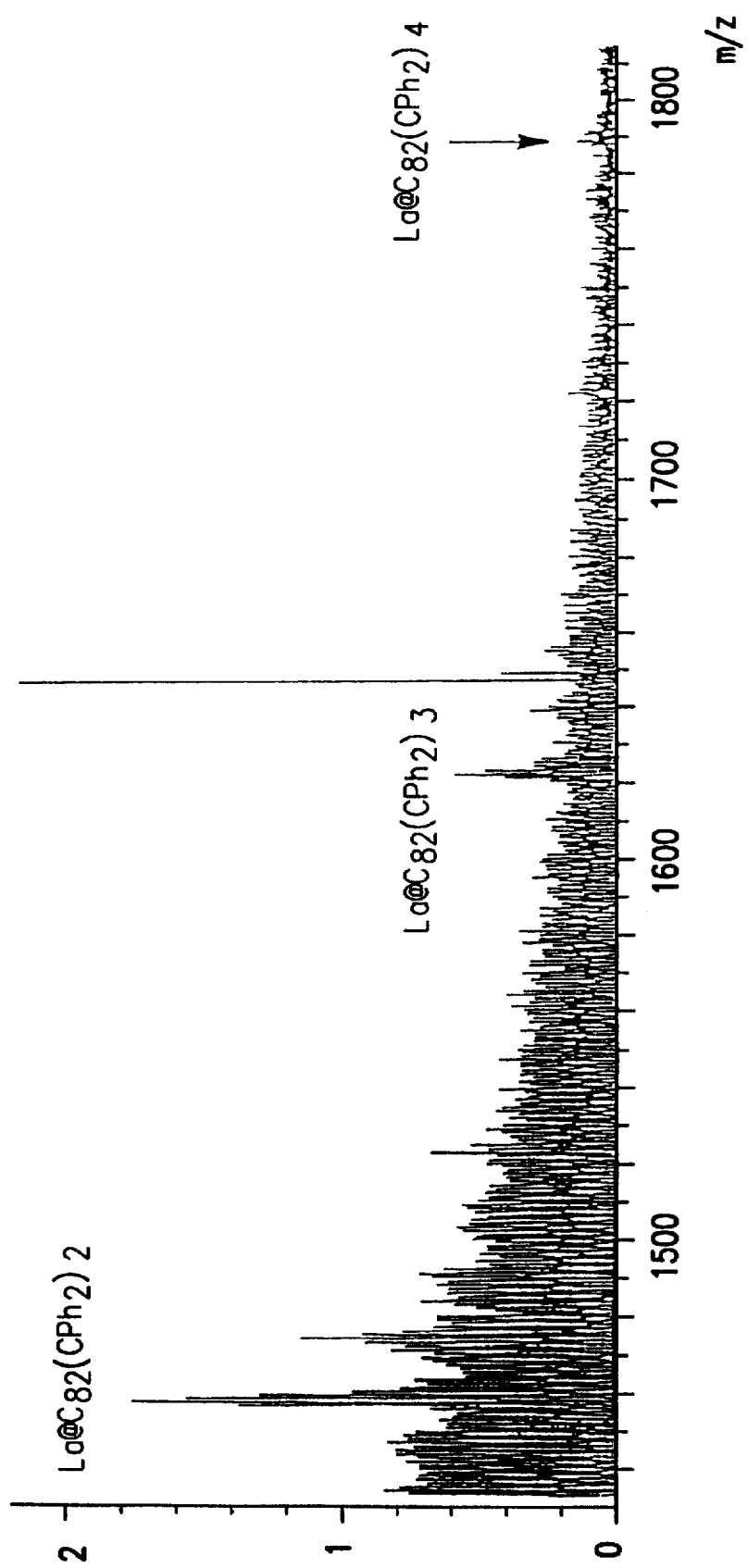
FIG. 5 is a diagram of a mass spectrum (mass range m/e=1430–1810) of a reaction product comprising compound (3) (at 210 minutes). In the figure, the horizontal axis is mass number and the vertical axis is relative ion intensity.

In the mass spectrum of FIG. 5 (mass range m/e= 1430–1810), in addition to the molecular ion peaks of the 1:2 adduct and 1:3 adduct, molecular ion peaks of a 1:4 adduct were observed from 1787 to 1793. This confirms the production of a compound La@$C_{82}$(C$Ph_2$)$_4$.

When two or more diphenylmethylenes (C$Ph_2$) are added to La@$C_{82}$, structural isomers having various positional relationships in the methylenes are produced. As the electron spin resonance absorptions of these isomers might be expected to be slightly different in position and spacing, the overall absorption is likely to be a broad peak. The broad absorption signals as the background in FIG. 1(E) probably correspond to compounds in which two or more of these substituent groups have been added.

According to this invention, a novel derivative of a metal-encapsulated fullerene having a side chain in which carbon is directly bonded to the fullerene cage is provided. This novel metal-encapsulated fullerene compound will no doubt find wide application as a functional material, superconducting material, electronics material or pharmaceutical material.

While there has been described what are at present considered to be preferred embodiments of the invention, it will be understood that various modifications may be made thereto, and it is intended that the appended claims cover all such modifications as fall within the true spirit and scope of this invention.

What is claimed:

1. A metal-encapsulated fullerene compound having the following structure:

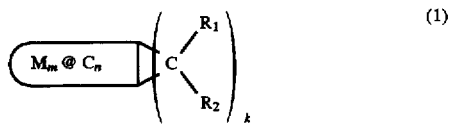

wherein:

M is a metal atom, m is an integer from 1 to 3, n is an even number from 28 to 200, k is an integer from 1 to 4, and $R_1$, $R_2$ are hydrogen, alkyl or aryl groups, but contain no active hydrogen.

2. A derivative of a metal-encapsulated fullerene compound as defined in claim 1 wherein:

said encapsulated metal atom M is at least one metal chosen from a group comprising alkali metals, alkaline earth metals, transition elements, lanthanoid elements and actinoid elements.

3. A compound for use as a magnetic resonance relaxant in MRI wherein said metal M encapsulated in the metal-encapsulated fullerene compound derivative according to claim 1 is gadolinium.

4. A method of synthesizing a metal-encapsulated fullerene compound by adding functional groups to a metal-encapsulated fullerene, wherein:

a diazomethane or substituted diazomethane to cycloaddition of a metal-encapsulated fullerene compound, and a denitrification reaction is performed to give a derivative of a metal-encapsulated fullerene compound:

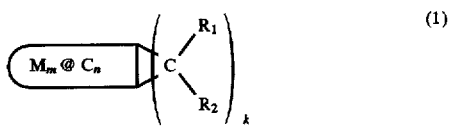

wherein $R_1$, $R_2$ are hydrogen, alkyl or aryl groups, or their substituents, but comprise no active hydrogen.

5. A method of synthesizing a derivative of a metal-encapsulated fullerene compound as defined in claim 4, comprising:

a dissolution step wherein said metal-encapsulated fullerene and said diazomethane or said substituted diazomethane are dissolved in a reaction solvent to prepare a reactant solution, a degassing step wherein dissolved gas is removed from said reactant solution by freeze degassing, and a reaction step wherein said reactant solution is heated so as to cause said diazomethane or said substituted diazomethane to react with said metal-encapsulated fullerene in said reactant solution.

6. A method of synthesizing a derivative of a metal-encapsulated fullerene compound as defined in claim 5, wherein:

the heating temperature of said reaction step in which said metal-encapsulated fullerene and said diazomethane are reacted, lies within the range of 30° to 100° C.

7. A method of synthesizing a derivative of a metal-encapsulated fullerene compound as defined in claim 5, wherein:

the heating temperature of said reaction step in which said metal-encapsulated fullerene and said diazomethane are reacted, is approximately 100° C.

8. A method of synthesizing a derivative of a metal-encapsulated fullerene compound as defined in claim 5, wherein:

said reaction solvent is at least one type chosen from aromatic hydrocarbon solvents and halogenated aromatic hydrocarbon solvents.

* * * * *